United States Patent [19]

DesMarais

[11] 4,323,534

[45] Apr. 6, 1982

[54] EXTRUSION PROCESS FOR THERMOPLASTIC RESIN COMPOSITION FOR FABRIC FIBERS WITH EXCEPTIONAL STRENGTH AND GOOD ELASTICITY

[75] Inventor: Thomas A. DesMarais, Norwood, Ohio

[73] Assignee: The Procter & Gamble Company, Cincinnati, Ohio

[21] Appl. No.: 104,260

[22] Filed: Dec. 17, 1979

[51] Int. Cl.$^3$ .............................................. B28B 3/20
[52] U.S. Cl. ............................ 264/176 R; 264/176 F; 264/211; 264/300; 264/344; 525/95; 524/536; 524/322; 524/385
[58] Field of Search .................. 264/49, 176 R, 176 F, 264/2 M, 300, 344; 525/95; 260/23 S, 33.4 PQ

[56] References Cited

U.S. PATENT DOCUMENTS

| | | | |
|---|---|---|---|
| 2,638,460 | 5/1953 | Crouch | 260/23.7 M |
| 3,198,868 | 8/1965 | Pedvetti et al. | 264/236 |
| 3,440,304 | 4/1969 | Hall et al. | 264/236 |
| 3,507,934 | 4/1970 | Minov et al. | 525/271 |
| 3,536,796 | 10/1970 | Rock | 264/49 |
| 3,600,309 | 8/1971 | Losey et al. | 264/236 |
| 3,632,540 | 1/1972 | Unmuth et al. | 525/95 |
| 3,842,154 | 10/1974 | Lundbeug et al. | 264/294 |
| 3,847,854 | 11/1974 | Cantev et al. | 260/23.7 M |
| 3,915,912 | 10/1975 | Ishicawa et al. | 264/211 |
| 3,939,242 | 2/1976 | Lundenberg et al. | 264/211 |
| 4,010,128 | 3/1977 | Saggese et al. | 260/23.7 M |
| 4,198,983 | 4/1980 | Beckev et al. | 525/95 |

OTHER PUBLICATIONS

Shell Chemical Co. Technical Bulletin SC-65-75 "Kraton-Thermoplastic Rubber" 20 pages, 10-1975.
Shell Chem. Co. Technical Bulletin SC-72-75 "Solution Behavior of Kraton G Thermoplastic" 21 pages, 4-1975.

Primary Examiner—Jay H. Woo
Attorney, Agent, or Firm—Fredrick H. Braun; Richard C. Witte; Monte D. Witte

[57] ABSTRACT

The object of this invention is to provide a composition of thermoplastic rubber which can be extruded into fibers and films with exceptional strength and good elasticity. Current formulations of some thermoplastic rubbers cannot be extruded into fibers or films with the accompanying strength and elasticity.

Compositions of the current invention comprise 20 to 50% by weight of one of a group of fatty acids or fatty alcohols containing from about 12 to about 24 carbon atoms and 80 to 50% by weight of a member selected from the group consisting of A-B-A block copolymers, where B is poly(ethylenebutylene) and A is a thermoplastic polymer which is phase incompatible with B.

This composition of matter results in a thermoplastic rubber composition that is easily extrudable into fibers or films. Extruded fibers of the current composition can be made into elastic fabrics, elastic bands for clothing or made into nonwoven structures for use in elastic bandages or wrapping. Films of the new composition can be used to make articles such as elastic disposable diaper backsheets or shower caps.

10 Claims, 1 Drawing Figure

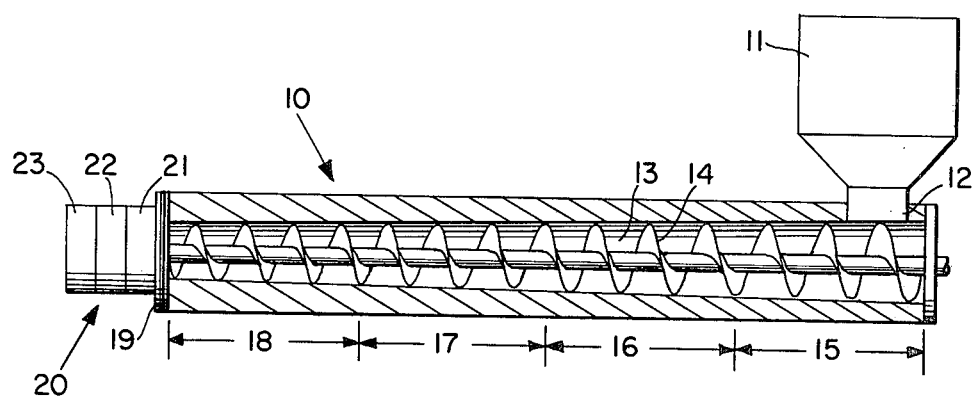

EXTRUSION PROCESS FOR THERMOPLASTIC RESIN COMPOSITION FOR FABRIC FIBERS WITH EXCEPTIONAL STRENGTH AND GOOD ELASTICITY

TECHNICAL FIELD

This invention relates to a new composition of matter for a thermoplastic rubber composition that is particularly well suited for the extrusion of fibers and films. The invention is also directed towards extruded elastic fibers, webs and films made of thermoplastic rubber having exceptional strength and good elasticity.

In the manufacture of fibers, webs and films from thermoplastic rubber, it has been shown that extrusion processes ease the manufacturing effort, are particularly economical and provide added occupational safety in a production process. However, the use of extrusion processes has proven particularly difficult with some thermoplastic rubbers, because during the extrusion process the extruded product will melt fracture and not form the fibers or films desired. The formulation of the current invention is of thermoplastic rubber which is easily extruded and which is useful for forming fibers and films to be made into end products incorporating the advantages of the rubber.

BACKGROUND ART

The background art discloses prior formulations of rubbers for use in the rubber industry.

The background art shows use of Kraton in a number of rubber formulations. In U.S. Pat. No. 4,010,128 issued to Saggese et al. on Mar. 1, 1971 is disclosed use of Kraton rubber in printing plates. U.S. Pat. No. 3,507,934 issued to Minor et al. on Apr. 21, 1970 discloses the basic composition and method of manufacture for Kraton rubbers having a general form of an A-B-A block copolymer.

The incorporation of stearic acid into thermoplastic rubber compositions is taught in U.S. Pat. No. 4,010,128 issued to Saggese et al. on Mar. 1, 1977. Saggese et al. discloses mixing up to 10% by weight stearic acid with thermoplastic polymers including Kraton rubbers.

The use of stearic acid in combination with thermoset rubbers is taught in U.S. Pat. No. 3,882,062 issued to Aron on May 6, 1975 where up to 2% by weight stearic acid is mixed with natural rubbers. U.S. Pat. No. 4,039,506 issued to Gessler et al. on Aug. 2, 1977 teaches the use of up to 1% by weight stearic acid with thermoset rubber compositions. U.S. Pat. No. 4,046,834 issued to Lee et al. on Sept. 6, 1977 discloses use of up to 2% stearic acid with finely divided vulcanized rubber having a composition of approximately 90% styrene butadiene rubber. U.S. Pat. No. 2,638,460 issued to Couch on May 12, 1953 discloses use of up to 2% stearic acid with butadiene-styrene thermoset rubbers.

DISCLOSURE OF THE INVENTION

In accordance with the present invention, there is provided a novel composition for use in extrusion of fibers and films comprising about 20% to about 50% by weight of a fatty chemical selected from the group consisting of fatty alcohols containing from about 12 to about 24 carbon atoms and fatty acids containing about 12 to about 24 carbon atoms and 80% to 50% by weight of a thermoplastic rubber that is an A-B-A block copolymer where A is a thermoplastic polymer and B is poly(ethylene-butylene). An example of such rubber is Kraton G rubber as described in the November 1975 Technical Bulletin SC: 72–75 of the Shell Chemical Co. hereby incorporated by reference.

The invention also includes the composition as disclosed above wherein the fatty acid used is stearic acid.

The invention also includes the composition as disclosed above wherein the A-B-A block copolymer is 30% polystyrene by weight and 70% by weight is poly(ethylene-butylene).

The invention also includes the composition as disclosed above wherein the composition includes 20 to 33% by weight of one of the group consisting of fatty alcohols having from about 12 to about 24 carbon atoms or fatty acids having from about 12 to about 24 carbon atoms.

The invention disclosed herein includes a process to make elastic products comprising the first step of mixing a composition of 20 to 50% by weight of one of the group of fatty acid or fatty alcohols having from about 12 to about 24 carbon atoms and 80% to 50% by weight of a member selected from the group consisting of A-B-A block copolymers, where A is polystyrene and B is poly(ethylene-butylene). This mixture is then extruded into fibers in a second step.

The invention disclosed herein includes a process to make film. The process involves a first step of mixing a composition of 20% to 50% by weight of one of the group of fatty acids or fatty alcohols having from about 12 to about 24 carbon atoms and 80% to 50% by weight of a member selected from the group consisting of A-B-A block copolymers, where B is poly(ethylene-butylene) and A is a thermoplastic polymer which is phase incompatible with B. In a second step, the mixture is then extruded into a film.

The invention disclosed herein optionally includes a process where the fibers or film made from the composition of matter is leached in isopropyl alcohol to remove fatty acid or fatty alcohol contained in the extruded fiber or film.

DESCRIPTION OF THE DRAWINGS

The process of the instant invention uses the equipment shown on the drawing which discloses a side cross-sectional schematic view of extrusion apparatus used in the process of the current invention.

DESCRIPTION OF THE INVENTION

The present invention involves a novel composition of matter for use in making fibers and films and a method to make fibers and films. Fibers resulting from this composition and process can be used to make elastic fibers for use in elastic bands in clothing, formed into nonwoven structures which can be useful in semi-disposable undergarments due to their soft hand and excellent elasticity and made into nonwoven structures for use in elastic bandages and wrappings. Films of the new composition can be used for stretchable disposable backsheets for diapers or elastic closures, shower caps, or other conventional uses wherein elastic films are desirable.

The composition of matter of the current invention is to be used in the manufacture of thermoplastic rubber fibers and thermoplastic rubber films comprises about 20% to about 50% by weight of a compound selected from the group consisting of fatty alcohols containing from about 12 to about 24 carbon atoms and fatty acids containing about 12 to about 24 carbon atoms and 80% to 50% by weight of a thermoplastic rubber that is an A-B-A block copolymer where B is poly(ethylene-butylene) and A is any thermoplastic polymer which is phase incompatible with B. Preferably, A is polystyrene. An example of such rubber is Kraton G rubber as described in the November 1975 Technical Bulletin SC: 72-75 of the Shell Chemical Co. hereby incorporated by reference. In a second embodiment, the A component is poly(alpha-methylstyrene).

A preferred embodiment of the composition contains 20% to about 33% by weight fatty acid or fatty alcohol.

In the composition of matter disclosed herein, A-B-A block copolymers that are particularly useful are those of Kraton G rubber (Kraton G is a trademark of the Shell Chemical Company, One Shell Plaza, P.O. Box 2463, Houston, Tex. 77001). In this composition of matter, Kraton G-1650 and Kraton G-1652 have been used with good results. Of the two rubbers, Kraton G-1652 has the lower molecular weight, although other rubbers having similar molecular weights are also useful.

In a particularly preferred embodiment of the composition of the current invention, stearic acid, a $C_{18}$ carbon atom fatty acid, is the preferred fatty acid to be used and Kraton G-1652 is the preferred thermoplastic rubber. In the formulations of Kraton G used, Kraton G is an A-B-A block copolymer where A represents a polystyrene segment and B represents a random copolymer of ethylene and butylene referred to as ethylene-butylene rubber. The Kraton G molecule is preferably 30% polystyrene by weight.

Among available thermoplastic rubbers, formulations of Kraton G thermoplastic rubber are not easily extruded into either fibers or films for use in manufacture of the finished products. The compositions of the present invention utilizing Kraton G rubber are easily extruded into fibers or films. While not wishing to be bound by any one theory concerning the operation of the present invention, it is believed that formulations of the composition described in the current invention are easily extruded into fibers or films because the fatty acid or fatty alcohol component solublizes the Kraton G molecules and, in particular, the B components of the block copolymer at extrusion temperatures. At extrusion temperatures, i.e., above 100° C., the A components of the block copolymer are easily extruded, however the Kraton G structure is too viscous to be extruded alone without substantial melt fracture of the product. In solution, the fatty component solublizes the B block of the copolymer, i.e., it coats the block to allow it to move more easily over surrounding molecules of the rubber, to allow the molecules to reorient themselves during extrusion.

Physical properties of the single fibers made from the compositions disclosed herein are disclosed in Tables 1 through 5 below. The fibers made from the compositions disclosed herein were extruded through a nosepiece having a multiplicity of 0.017 inch (4.32×10⁻⁴ m) orifices spaced 0.050 inch (0.127 cm) apart. The resulting fibers have a diameter of at least 0.010 inch (2.54×10⁻⁴ m) with an average diameter of 0.012 inch (3.08×10⁻⁴ m).

The tensile strength, elongation percent and tenacity of fibers of the compositions listed produced by the extrusion method disclosed herein are shown in the tables below. Tensile strength, elongation percent and tenacity are measured with the following method. Four samples of 5 inch (12.7 cm) lengths of fiber are weighed to the nearest 0.1 mg on an analytical balance. Ends of the fiber are placed in a 1 inch (2.54 cm) length of 2 millimeter I.D. latex tubing. The ends, encased in tubing, are set in the jaws of an Instron Pneumatic Action Clamp, Model 3B, under 60 psi (4.22 kg/cm³) clamping pressure in a ⅜ inch (0.9525 cm) clamping bar. The clamping bar is attached to an Instron testing machine, Model 1122, made by Instron Corporation, 2500 Washington Street, Canton, Mass. 02021. The Instron machine is set with a gauge length of 2 inches (5.08 cm), at a crosshead speed and chart speed of 20 inches per minute (50.8 cm/minute) and a loadcell setting in the 100 to 2,000 gram range. The testing machine then elongates the fiber, recording breaking load and percent elongation. Tensile measurements are reported from an average of four readings. Percent elongation is reported with an average of four readings. Tenacity is derived from the above measurements and is expressed in grams per denier. Tenacity is calculated with the following formula:

$$\text{Tenacity} = \frac{\text{Tensile (pound} \times 454)}{\text{Milligrams per inch} \times 354.331}$$

The stress relaxation and set of fiber of the composition of the current invention can be measured through the following method: Five pieces of 5 inch (12.7 cm) fiber are cut from a sample of material. Two 1 inch (2.54 cm) lengths of 2 millimeter I.D. latex tubing are slipped on the ends of the fiber samples. The ends of the fiber in the latex tubing are set in an Instron Pneumatic Action Clamp, Model 3B, under 60 psi (4.22 kg/cm²) clamping pressure in a ⅜ inch (0.9525 cm) clamping bar mounted on an Instron testing machine. The Instron testing machine is set at a gauge length of 2 inches (5.08 cm) having a crosshead speed and chart speed of 20 inches (50.8 cm) per minute. The load cell may be set in the 100 to 2,000 grams range. The fiber in the Instron machine is cycled from 0% elongation to 100% elongation five times. At the end of the fourth extension and beginning on the fifth extension, the recorder is activated. On the fifth extension, the crosshead is stopped at maximum extension for 30 seconds. The Instron machine records the decrease in load on the fifth extension during the 30 second hold at 100% extension. At the end of 30 seconds, the fiber is returned to 0% elongation and held for 30 seconds. Then the crosshead is moved till the sample is taut. The Instron machine also records the maximum load at the fifth extension and the distance the crosshead moves from 0 extension until the sample is taut. The percent stress relaxation can then be calculated from the following formula:

$$\% \text{ Stress Relaxation} = \frac{\text{Decrease in Load at 100\% during the fifth extension}}{\text{Maximum Load on fifth extension}} \times 100$$

The percent set can then be measured through the following equation:

$$\% \text{ Set} = \frac{\text{Increase in sample length}}{\text{Gauge length}} \times 100$$

The results of these tests are disclosed in the tables below. Compositions shown are weight percent of the final product.

TABLE 1

Physical Properties of Kraton G-1652 in combination with different fatty acids and a fatty alcohol - single fiber analysis

| Additive | Level In Resin | Tenacity (grams/ denier) | Elongation At Break (%) | Stress Relaxation (%) | % Set |
|---|---|---|---|---|---|
| Stearic acid | 25% | 0.6 | 670 | 21 | 26 |
| Palmitic acid | 25% | 0.75 | 650 | 18 | 16 |
| Cetyl alcohol | 25% | 0.6 | 523 | 19 | 9 |
| Stearic acid | 20% | 0.9 | 594 | 16 | 7 |

TABLE 2

Physical Properties of Kraton G-1650 in combination with different levels of stearic acid - single fiber analysis

| Stearic Acid Level | Tenacity (grams/ denier) | Elongation At Break (%) | Stress Relaxation (%) | % Set |
|---|---|---|---|---|
| 33% | 0.8 | 657 | 26 | 26 |
| 25% | 0.66 | 770 | 17 | 15 |

An example of fibers with good strength and elasticity can preferably be made from a composition of the following: 79.13% Kraton G-1652; 19.78% stearic acid; 0.98% titanium dioxide and 0.1% antioxidant (all percentages are weight percents). The titanium dioxide, added for coloring, and antioxidant are conventional additives.

The physical properties of the extruded rubber composition of the current invention can be improved by leaching out substantially all the fatty chemicals after extrusion by soaking the extruded product in alcohols that have good solubility for fatty chemicals. The results of leaching are shown below. The leaching of fatty chemicals from extruded rubber results in a final rubber product having a lower percent set and lower stress relaxation values; the rubber is a more "snappy" rubber. Reduction in the stress relaxation values and percent set and improved tenacity result from the removal of fatty acids from the compounded rubber. At room temperature, fatty chemicals, i.e., stearic acid, are a solid and the components yield a rubber composition containing solid particles. The solid particles impede elastic movement of rubber molecules in the solid composition at room temperature and thus adversely effect both stress relaxation and percent set. The leaching process removes and reduces the size of large fatty chemical particles which would otherwise impede the stress relaxation and percent set of a rubber. The fatty chemicals are preferably leached out in a 10:1 isopropyl alcohol:rubber mixture.

TABLE 3

Physical Properties of Kraton G-1652/fatty acid or alcohol combinations - single fiber analysis after removing the fatty acid or fatty alcohol using isopropyl alcohol extraction

| Additive | Level Before Extraction | Level After Extraction | Tenacity (grams/ denier) | Elongation At Break (%) | Stress Relaxation (%) | % Set |
|---|---|---|---|---|---|---|
| Stearic acid | 20% | 0.9% | 0.8 | 552 | 12 | 7 |
| Cetyl alcohol | 25% | 15% | 0.7 | 532 | 15 | 7 |

TABLE 4

Physical Properties of Kraton G-1650/stearic acid combinations - single fiber analysis after removing the acid using isopropyl alcohol extraction

| Stearic Acid Level Before Extraction | Level After Extraction | Tenacity (grams/ denier) | Elongation At Break (%) | Stress Relaxation (%) | % Set |
|---|---|---|---|---|---|
| 33% | 0.75% | 0.5 | 615 | 17 | 7 |
| 25% | — | 1.0 | 990 | 12 | 6 |

Table 5 shows the properties of a specific composition of the present invention wherein after extrusion, fatty chemicals are extracted from the fibers by leaching in isopropyl alcohol in proportions of 10 parts alcohol to 1 part extruded rubber. These fibers have substantial amounts of the fatty chemicals mixed in the composition removed by leaching with isopropyl alcohol. The fiber composition contains conventional additives to add color and prevent oxidation of the composition.

TABLE 5

Physical Properties of a Kraton G-1652/stearic acid mixture with two common additives, $TiO_2$ pigment[1] and Irganox[R] 1010 anti-oxidant[2] extracted with isopropyl alcohol, and as made

| | % Stearic Acid | Tenacity (grams/ denier) | Elongation At Break (%) | Stress Relaxation (%) | % Set |
|---|---|---|---|---|---|
| As Made | 20% | 0.8 | 551 | 16 | 8 |
| After Leaching | 1.1% | 1.2 | 510 | 13 | 7 |

Notes:
[1]$TiO_2$ at 1.5%
[2]Irganox[R] 1010 at 0.1%

The composition of the present invention allows one to extrude thermoplastic rubbers into film. As stated above, the preferred composition containing Kraton G cannot be extruded by itself because the extrusion will melt fracture after being emitted from the extrusion dye. Extruded films of the present composition can be made without the expense of being cast from a solution that uses substantial amounts of solvents, such as toluene. Therefore, extruded films are substantially less expensive than solvent cast films and can be made without the use of expensive venting equipment during the manufacture.

The thermoplastic nature, easy processibility and high strength characteristics make these compositions preferred materials for melt blown elastic webs, very thin films and fibers. Molded parts can also be made by compounding the ingredients, heating to a range of about 380° F. (195° C.) to about 400° F. (240° C.) and molding the part in an injection molding apparatus, but use of the present composition is less desirable for use in making injection molded parts as it is more difficult to leach out fatty acids through the thick sections of the molded parts. The composition is best suited for use in conjunction with extruders and known injection molding apparatus.

PROCESS

The first step of general process for making the articles of the composition of the current invention involves mixing the starting materials of thermoplastic rubber and the fatty acid or fatty alcohol that will make up the composition. Starting materials can also include conventional additives such as pigments, antioxidants, and other common additives which are nonreactive with the components of fatty acid or fatty alcohol used. The mixture of materials is then extruded into the desired final form of films, fibers, or molded articles. The thermoplastic rubber and fatty acids or alcohols can be mixed in well known in-line mixing equipment.

The composition of the current invention can be extruded from and components mixed in extruder 10 shown in schematic cross-sectional view in the drawing. In the mixing phase, the components of the composition are fed into hopper 11 and through chamber inlet 12 into extrusion chamber 13. Axially disposed within extrusion chamber 13 is a screw 14 which advances material from inlet 12 to the extrusion dies 20. While screw 14 turns, the material will advance through heat zones 15, 16, 17 and 18 which will progressively heat material in the extrusion chamber 13 to the extrusion temperature. Screw 14 both moves the material through the extrusion chamber 13 while applying a uniform pressure to the material to be extruded.

At the forward end of extrusion chamber 13 is gate 19 which faces on extrusion die 20. Extrusion die 20 has three sections 21, 22, and 23 which are individually heated along with gate 19 to finally put the material to be extruded at proper extrusion temperature in a range of 380° F. (195° C.) to 460° F. (240° C.). The extruded material will emerge from extrusion die 20 in the physical shape which is desired, such as rods of compounded material or final finished shapes, such as fibers or film. The final extrusion temperature will vary with the finished product, however, the temperature may vary ±30° F. (±17° C.) over the center lines listed in the examples below.

The preferred procedure for compounding the composition is in a conventional in-line mixer or in the process recited below. The thermoplastic rubbers, fatty chemicals and other desired additives are mixed in a twin shell dry blender, such as Model L-B 5056 manufactured by The Patterson-Kelley Co., Inc., East Stroudsburg, Pa. Mixing is performed on a 2500 gram batch for two minutes. The mixture is fed into a plastic extruder as shown in the drawings such as NRM Pacemaker III 2½" (6.35 cm) Extruder 10 equipped with "polyethylene" screw 14; a 3.2/1 compression ratio, 24/1 L/D screw turning at 30 RPM, all manufactured by NRM Corporation, 180 S. Avenue, Talmadge, Ohio 44278. The mixture is compounded when ¼-⅛" (0.635–0.3175 cm) diameter strands are extruded and are collected by any convenient means, such as by passing through a water bath chiller, after which the strands are collected in containers and allowed to cool in the air. The strands are chopped by feeding them into a granulator, such as 2069-SP granulator manufactured by IMS Co., 24050 Commerce Park Rd., Cleveland, Ohio 44122. Various screens are available so that any size pellet can be made during the granulation phase. Extruder conditions are typically as follows:

| Temperature profile: | Zone 15 - 300° F. (149° C.) |
| --- | --- |
| | Zone 16 - 400° F. (204° C.) |
| | Zone 17 - 400° F. (204° C.) |
| | Zone 18 - 400° F. (204° C.) |
| | Gate 19 - 410° F. (210° C.) |
| | Die 20 - 410° F. (210° C.) |
| Screw speed: 50 RPM | |

The final extrusion temperature is in a range of 380° F. (195° C.) to 440° F. (228° C.). This first extrusion step compounds and mixes the components thoroughly. The granules are subsequently extruded into a desired final form of fibers, films or webs.

FIBER FORMING

An especially useful fiber results from extrusion of a compounded resin comprising 79.13% Kraton G-1652; 19.78% stearic acid (Emersol 153, 95% Stearic Acid from Emery Industries, Cincinnati, Ohio); 0.98% Titanium Dioxide (OR-450 Unitane made by American Cyanamid Company, Bound Brook, N.J. 08805); and 0.1% Irganox 1010 Antioxidant (CibaGeigy, Ardsley, N.Y. 10502). After compounding, the mixture was fed into an extruder, such as the ⅝" (1.5875 cm) Wayne Extruder, with a 3:1 compression ratio screw L/D 20:1 (Made by Wayne Machine & Die Co., 100 Furler Street, Totowa, N.J.) fitted with a 4" (10.16 cm) section (closed on the ends) melt-blowing die. The resin composition was extruded through a box provided with hot air inlets and a slit through which the resin, in the form of fibers, and the hot air exits, as is taught in U.S. Pat. No. 3,825,380 issued on July 23, 1974 to Harding, hereby incorporated by reference. The extruder screw turned at 30 RPM and had a temperature in a first heating zone of 320° F. (160° C.) and in a second heating zone of 390° F. (198.9° C.). Air was blown into the extrusion block at the rate of 100 SCF/Hr/Side (2832 letters STP/side) at a temperature of 500° F. (260° C.). Individual fibers were extruded from the melt-blowing die.

FILM FORMING

The composition of the materials disclosed herein is particularly well-suited for use in making extruded films. For example, a composition useful for making films is made of 75% by weight of a thermoplastic rubber such as Kraton G-1652 and 25% by weight stearic acid. Granules of the composition were made as in the above noted process and subsequently extruded in an apparatus like that shown in FIG. 1. The granules were then fed into a plastic extruder such as an NRM Pacemaker III 2½" (6.35 cm) extruder available from NRM Corporation, 180 S. Avenue, Talmadge, Ohio 44278. The extruder was equipped with a film die such as the Johnson Flex-Lip 24" (60.96 cm) film die made by Johnson Plastics Machinery Co., 1600 Johnson Street, Chippewa Falls, Wis. 54729. The film was taken from the film die on a suitable take-up reel and casting roll chilled with water. The temperature profile in the extruding machine with reference to FIG. 1 was as specified in the table below.

| Temperature profile: | Zone 15 - 390° F. (199° C.) |
| --- | --- |
| | Zone 16 - 450° F. (232° C.) |
| | Zone 17 - 450° F. (232° C.) |
| | Zone 18 - 450° F. (232° C.) |
| | Gate 19 - 410° F. (210° C.) |
| Die 20 | Zone 21 - 410° F. (210° C.) |
| | Zone 22 - 420° F. (215° C.) |
| | Zone 23 - 430° F. (221° C.) |
| Screw speed: 50 | |
| Die opening: 0.030" (0.0762 cm) | |

The final extrusion temperature may vary within the range of 400°–460° F. (207°–240° C.) without appreciable differences in the physical properties. The resulting film was drawn to achieve 1 mil film (25.4 microns) thickness. The stearic acid was extracted from the resultant film by leaching with isopropyl alcohol at room temperature for one hour resulting in films that are "snappy" and thin. The leaching is carried out in proportions of about 10 parts isopropyl alcohol to 1 part extruded film.

WEB FORMING

The composition of the current invention is particularly well-suited for being extruded into fibers for use in making webs. An especially useful web resulted from extrusion of a compounded resin comprising 79.13% Kraton G-1652; 19.78% stearic acid (Emersol 153, 95% Stearic Acid from Emery Industries, Cincinnati, Ohio); 0.98% Titanium Dioxide (OR-450 Unitane made by American Cyanamid Company, Bound Brook, N.J. 08805); and 0.1% Irganox 1010 Antioxidant (Ciba-Geigy, Ardsley, N.Y. 10502). This mixture was mixed in a twin shell dry blender such as Model L/P 5056 by The Patterson-Kelley Company. The resin was compounded as in the process described above. The compounded resin was fed into an extruder, such as the ⅝" (1.5875 cm) Wayne extruder, with a 3:1 compression ratio screw, L/D 20:1 (made by Wayne Machine & Die Co., 100 Furler Street, Totowa, N.J.) fitted with a 4" (10.16 cm) section (closed on the ends) melt-blowing die. The resin composition was extruded through a box provided with hot air inlets and a slit through which the resin, in the form of fibers, and the hot air exit. The extruder screw turned at 30 RPM and had a temperature in a first heating zone of 320° F. (160° C.) and in a second zone of 390° F. (198.9° C.). Air was blown into the extrusion block at the rate of 1150 SCF/Hr/Side (32568 L[STP]/side) at a temperature of 650° F. (343.3° C.). The extrusion nosepiece had orifices with a diameter of 0.017" (0.0432 cm) spaced 0.050" (0.127 cm) center to center. Extrusion lips were spread 0.12" (0.3048 cm) where the lip and the nosepiece were recessed in the extrusion box 0.14" (0.3556 cm). The fibers had a diameter of 5-20 microns with an average diameter of 10 microns and an average length of 2.0 inches. The fibers were matted together to form a web. As formed, the web had a tensile strength in the direction of machine formation of greater than 3 lbs./in./(oz./yd.$^2$) (22.56 g/cm/g/m$^2$) [as used herein the direction of machine formation is referred to as machine direction]. The web had a tensile strength perpendicular to the machine direction of greater than 0.5 lbs./in./(oz./yd.$^2$) [3.76 g/cm/(g/m$^2$)]. The web had a basis weight of 2.0 oz. or more/yd.$^2$.

It will be understood by those skilled in the art that the invention has been described with reference to exemplary embodiments and that variations and modifications can be effected from the described embodiments without departing from the scope and spirit of the invention. The invention is prescribed and limited by the claims which follow.

What is claimed is:

1. A process for making fibers comprising the steps of:
   (a) mixing a composition comprising:
      (i) from about 20% to about 50% by weight of a fatty chemical selected from the group consisting of fatty acids containing from about 12 to about 24 carbon atoms and fatty alcohols containing from about 12 to about 24 carbon atoms; and
      (ii) from about 80% to about 50% by weight of an A-B-A block copolymer wherein A is selected from the group consisting of polystyrene and poly(alpha-methylstyrene) and B is poly(ethylene-butylene);
   (b) heating said composition to a temperature of from about 195° C. to about 240° C.; and
   (c) extruding said composition into fibers.

2. The process of claim 1 wherein said composition comprises from about 20% to about 33% fatty chemical.

3. The process of claim 1 wherein said fatty chemical comprises stearic acid.

4. The process of claim 1 wherein said A-B-A block copolymer comprises about 30% by weight polystyrene.

5. The process of claim 1, 2, 3, or 4 wherein after said extruding step there is the step of leaching substantially all said fatty chemical from said fibers with alcohol having solubility for said fatty chemical.

6. A process for making films comprising the steps of:
   (a) mixing a composition comprising:
      (i) from about 20% to about 50% by weight of a fatty chemical selected from the group consisting of fatty acids containing from about 12 to about 24 carbon atoms and fatty alcohols containing from about 12 to about 24 carbon atoms; and
      (ii) from about 80% to about 50% by weight of an A-B-A block copolymer wherein A is selected from the group consisting of polystyrene and poly(alpha-methylstyrene) and B is poly(ethylene-butylene);
   (b) heating said composition to a temperature of from about 195° C. to about 240° C.; and
   (c) extruding said composition into films.

7. The process of claim 6 wherein said fatty chemical comprises stearic acid.

8. The process of claim 6 wherein said A-B-A block copolymer comprises about 30% by weight polystyrene.

9. The process of claim 6, 7, or 8 wherein after said extruding step there is the step of leaching substantially all said fatty chemical from said films with alcohol having solubility for said fatty chemical.

10. A process for making molded articles comprising the steps of:
    (a) mixing a composition comprising:
       (i) from about 20% to about 50% by weight of a fatty chemical selected from the group consisting of fatty acids containing from about 12 to 24 carbon atoms and fatty alcohols containing from about 12 to about 24 carbon atoms; and
       (ii) from about 80% to about 50% by weight of an A-B-A block copolymer wherein A is selected from the group consisting of polystyrene and poly(alpha-methylstyrene) and B is poly(ethylene-butylene);
    (b) heating said composition to a temperature of from about 195° C. to about 240° C.; and
    (c) extruding said composition through means for injection molding.

* * * * *